United States Patent [19]

Lese et al.

[11] 4,158,740

[45] Jun. 19, 1979

[54] OXIDATION OF BUTANE TO ACETIC ACID

[75] Inventors: Henri K. Lese, Monroeville; Francis E. Wynne, Allison Park, both of Pa.

[73] Assignee: Gulf Research & Development Company, Pittsburgh, Pa.

[21] Appl. No.: 890,608

[22] Filed: Mar. 20, 1978

[51] Int. Cl.$^2$ ............................................. C07C 51/20
[52] U.S. Cl. ...................................... 562/549; 203/94; 260/597 R; 560/241; 562/608
[58] Field of Search ............. 260/533 R, 541; 203/94; 562/549, 608

[56] References Cited

U.S. PATENT DOCUMENTS 4,032,570   1/1977   Schulz et al. .................... 260/533 R

OTHER PUBLICATIONS 1,020,797   2/1966   United Kingdom ........... 260/533R

Primary Examiner—Vivian Garner

[57] ABSTRACT

A process for converting butane to acetic acid wherein a mixture containing butane, molecular oxygen, acetic acid and cobaltic ions is continuously passed through a reaction zone under elevated temperatures and elevated pressures while maintaining therein a partial pressure of molecular oxygen of about 0.6 to about 15 pounds per square inch (0.04 to about 1.1 kilograms per square centimeter).

15 Claims, 1 Drawing Figure

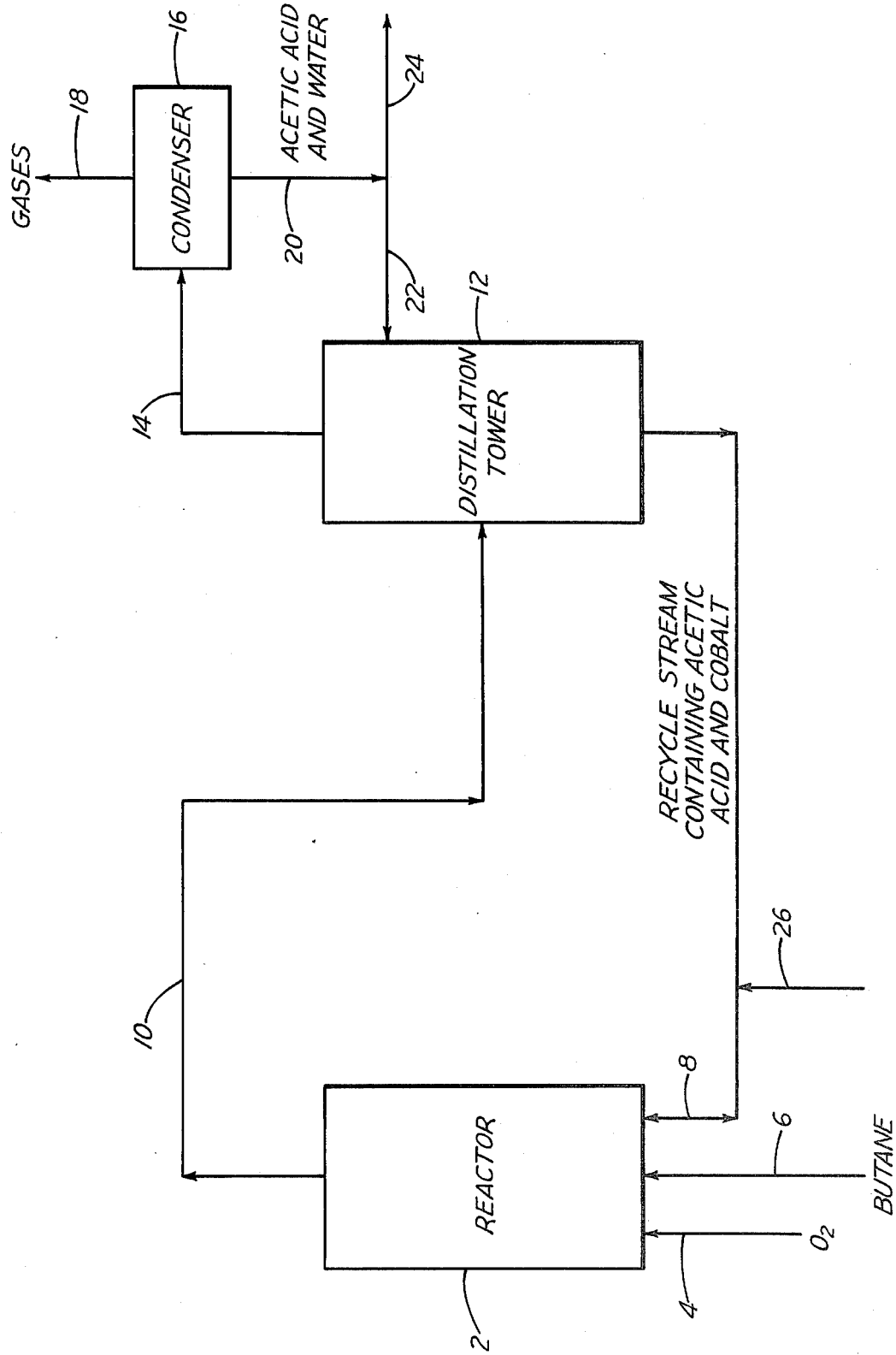

OXIDATION OF BUTANE TO ACETIC ACID

BACKGROUND OF THE INVENTION

1. Field of the Invention

This invention relates to a process for converting butane to acetic acid wherein a mixture containing butane, molecular oxygen, acetic acid and cobaltic ions is continuously passed through a reaction zone under elevated temperatures and elevated pressures while maintaining therein a partial pressure of molecular oxygen of about 0.6 to about 15 pounds per square inch (0.04 to about 1.1 kilograms per square centimeter).

2. Description of the Prior Art

It is known that butane can be converted by oxidation to acetic acid. However, known processes possess disadvantages in that conversion of butane and/or selectivity to acetic acid are low. This is shown, for example, in U.S. Pat. Nos. 2,653,962 to Mitchell et al. and 2,704,294 to Morgan, Jr., et al.

SUMMARY OF THE INVENTION

This invention relates to a process for converting butane to acetic acid in high conversions and high yields which comprises continuously passing a mixture containing butane, molecular oxygen, acetic acid and cobaltic ions through a reaction zone under elevated temperatures and elevated pressures while maintaining therein a partial pressure of molecular oxygen of about 0.6 to about 15 pounds per square inch (0.04 to about 1.1 kilograms per square centimeter).

BRIEF DESCRIPTION OF THE INVENTION

The process defined and claimed herein can be understood by reference to FIG. I. There is continuously introduced into reactor 2, molecular oxygen by way of line 4, butane by line 6 and a mixture containing acetic acid and cobaltic ions by line 8. Although molecular oxygen alone is preferred for use herein, any gaseous stream containing molecular oxygen, such as air, can also be used.

In the feed, the molecular oxygen to butane weight ratio will be in the range of about 0.1:1 to about 10:1, preferably from about 0.3:1 to about 3:1. The weight ratio of total material in line 8 to butane will be about 0.5:1 to about 15:1, preferably about 1:1 to about 10:1. The weight percent of cobalt, as cobalt metal, in line 8 will be about 0.1 to about 10 percent, preferably about one to about five percent. Of the cobalt in line 8, about 10 to about 90 weight percent, preferably about 20 to about 60 weight percent, must be in the form of cobaltic ions, that is, must exist in the valence state of +3, in order to obtain maximum conversion of butane and excellent yields of acetic acid in reactor 2.

In its passage through reactor 2 the reaction mixture is stirred and a liquid volume hourly space velocity (LHSV) of about 0.05 to 1.0, preferably about 0.1 to about 0.5 is maintained. The reaction temperature is maintained in the range of about 75° to about 130° C., preferably about 90° to about 120° C., and the total pressure in the range of about 200 to about 500 pounds per square inch absolute (about 14 to 35 kilograms per square centimeter), preferably about 285 to about 425 pounds per square inch absolute (about 20 to about 30 kilograms per square centimeter). However, in order to obtain extremely high conversions of butane and extremely high yields of acetic acid, it is critical that the partial pressure of the molecular oxygen be maintained throughout the reaction period within the range of about 0.6 to about 15 pounds per square inch (about 0.04 to about 1.1 kilograms per square centimeter), preferably within the range of about 0.6 to about six pounds per square inch (about 0.04 to about 0.4 kilograms per square centimeter).

At the end of the reaction period the reaction product is continuously removed from reactor 2 by line 10 and passed into distillation tower 12 wherein separation of the reaction product into selected portions thereof is effected as follows. In the distillation tower the pressure can be maintained in the range of about 15 to about 500 mm Hg, preferably in the range of about 15 to about 115 mm Hg. We have found that the temperature in the base of the distillation tower, that is, reboiler temperature, is critical and must be maintained within the relatively narrow temperature range of about 25° to about 80° C., preferably about 25° to about 65° C. This is so because we have found that at temperatures in excess thereof the cobaltic ions present in the reaction product tend to be converted to cobalt of a lower valence state, for example, cobaltous ions. Since in the preferred embodiment the cobalt catalyst is recycled to the reaction zone wherein a minimum level of cobaltic ions must be maintained therein, it is imperative that the cobaltic ions in the reaction product not be appreciably reduced to a lower valence state during distillation.

As a result of the distillation described above an overhead product, substantially gaseous, containing oxygen, CO, $CO_2$, butane, acetone, methyl acetate, ethyl acetate, methyl ethyl ketone, some water and some of the acetic acid is removed from the distillation tower by line 14 and is passed to condensor 16, which is maintained under conditions sufficient to condense acetic acid and water therein, for example, a temperature of about 3° to about 15° C. and a pressure of about 0.02 to about 0.15 pounds per square inch absolute (about 15 to about 115 mm Hg). The gases are removed from condensor 16 by line 18 and the acetic acid and water by line 20. A portion of the acetic acid and water is returned to distillation tower 12 by line 22 and the remainder is removed from the system by line 24.

The amount of gases removed by line 18 is small. Thus, the total grams of gases removed per gram of butane fed to reactor 2 will be in the range of about 0.05:1 to about 1:1, generally from about 0.4:1 to about 0.8:1. If desired, the butane in line 18 can be recovered and recycled to the reactor and/or the remaining compounds therein can also be recovered in any known manner. The grams of water per gram of butane fed to reactor 2 present in line 24 will be in the range of about 0.05:1 to about 0.5:1, generally about 0.1:1 to about 0.3:1, and the grams of acetic acid per gram of butane converted in reactor 2 will be in the range of about 1.4:1 to about 2.0:1, generally about 1.5:1 to about 1.8:1. The acetic acid and water in line 24 can be separated from each other, if desired, by any conventional means in order to recover the product acetic acid obtained herein. An important reason to remove water from the reaction system in line 24 is to reduce the amount of water in the recycle stream, defined below, so as not to adversely affect the reaction in reactor 2.

The remainder of the product in the distillation tower, in the preferred embodiment, is continuously removed from the base of distillation tower 12 by line 8 and constitutes the acetic acid and cobalt charge to reactor 2. Although acetic acid and cobalt have been identified as being present in line 8, there can be present some water, some of the following acids: propionic, butyric, succinic, adipic and glutaric and hydroxy esters. Water concentration can range from about 0.1 to about 10 weight percent, generally from about 0 to about five weight percent, while the combined esters and acids range from about one to about 20 weight percent, generally from about two to about 15 weight percent. The presence of the latter acids and hydroxy esters in line 8 is not detrimental and their amounts will stabilize within the defined parameters on continued operation. Any make-up catalyst, if needed, can be introduced into the system by line 26, for example, cobaltic salts of organic acids, such as acetic acid, propionic acid, butyric acid, naphthenic acids, etc.

DESCRIPTION OF PREFERRED EMBODIMENTS

EXAMPLE I

Two runs were carried out following the procedure of FIG. I, wherein molecular oxygen, butane and a recycle stream containing acetic acid and cobalt were continuously passed through a one-gallon (3.8 liters) stirred autoclave. The runs were identical except that the amount of molecular oxygen introduced were varied. The data obtained are summarized below in Table I.

TABLE I

| Operating Conditions | Run No. 1 | Run No. 2 |
|---|---|---|
| Temperature, °C. | 110 | 110 |
| Total Pressure, PSIA (Kg/Cm$^2$) | 365(25.7) | 365(25.7) |
| Partial Pressure of O$_2$, PSI (Kg/Cm$^2$) | 4.0(0.28) | 85.4(6.00) |
| Feed Rates, Grams/Hour | | |
| Oxygen | 106 | 113 |
| Butane | 148 | 148 |
| Catalyst Solution (Recycle) | 841 | 841 |
| Catalyst Solution Composition, Wt. % | | |
| Water | 3.9 | 3.9 |
| Acetone | 0.1 | 0.1 |
| Acetic Acid | 82.9 | 82.9 |
| Methyl Ethyl Ketone | 2.0 | 2.0 |
| Propionic Acid | 4.7 | 4.7 |
| Butyric Acid | 2.3 | 2.3 |
| Compound Identified As a Hydroxy Ester | 0.2 | 0.2 |
| Succinic Acid | 0.8 | 0.8 |
| Cobaltic Ion | 0.31 | 0.31 |
| Cobaltous Ion | 0.58 | 0.58 |
| Unidentified Components | 0.4 | 0.4 |
| LHSV | 0.27 | 0.27 |
| Results | | |
| Oxygen In Off-Gas | 0.7 | 16.5 |
| Acetic Acid Yield; G/Gm Butane Reacted | 1.64 | 1.41 |
| Acetic Acid Productivity Gm/Hour/Liter of Reactor Space | 24.0 | 14.4 |
| Oxygen Conversion, Per Cent | 99 | 86 |
| Butane Conversion, Per Cent | 45 | 27 |

The data in Table I emphasizes the criticality of maintaining the partial pressure of molecular oxygen within the defined limits. Note that in Run No. 1 the oxygen partial pressure was maintained within the defined limits but not in Run No. 2. In Run No. 1 the acetic acid yield, the acetic acid productivity, the oxygen conversion and the butane conversion were all greatly superior to the results obtained in Run No. 2. This is totally unexpected, since the increased oxygen availability in Run No. 2 to hydrocarbon oxidation would be expected to result in increased hydrocarbon oxidation.

EXAMPLE II

This run shows the criticality of maintaining a reboiler temperature during distillation between about 25° to about 80° C. in order to assure that the effective cobaltic ions, which serve as catalyst herein, are not reduced to the lower, undesirable lower valence state ineffective as catalyst herein.

Table II below summarizes results obtained when an acetic acid solution containing cobalt dissolved therein was subjected to a temperature of 85° C. for a period of four hours.

TABLE II

| Time, Hours | Total Cobalt, As Metal, Weight Per Cent | Total Cobaltic Ions, Weight Per Cent* |
|---|---|---|
| 0 | 0.35 | 0.14 |
| 2 | 0.35 | 0.03 |
| 4 | 0.34 | 0.01 |

*Remainder believed to be cobaltous ions.

It can be seen from the data in Table II that at the end of two hours the weight percent cobaltic ions present had been reduced to 0.03 percent, an unacceptable level of catalyst for use in a recycle stream. At the end of four hours substantially no cobaltic ions were present in the product.

EXAMPLE III

This run shows that by operating in accordance with the preferred embodiment defined and claimed herein the cobaltic ion level in the recycle can be maintained at an acceptable catalyst level. During the operation of Run No. 1 in Example I above the distillation tower was operated at a pressure of 70 mm Hg, with the temperature at the top of the distillation tower being 53° C., the middle 55° C. and the bottom, or reboiler, 63° C. Throughout the operation, the total cobalt metal content in the recycle stream was 0.89 weight percent, with the cobaltic ion content being 0.31 weight percent.

Obviously, many modifications and variations of the invention, as hereinabove set forth, can be made without departing from the spirit and scope thereof, and therefore only such limitations should be imposed as are indicated in the appended claims.

We claim:

1. A process for converting butane to acetic acid which comprises continuously passing a reaction mixture containing butane, molecular oxygen, acetic acid and cobaltic ions through a reaction zone under elevated temperatures in the range of about 75° to about 130° C. and elevated pressures in the range of about 200 to about 500 pounds per square inch absolute while maintaining therein a partial pressure of molecular oxygen of about 0.6 to about 15 pounds per square inch.

2. The process of claim 1 wherein said partial pressure of molecular oxygen is in the range of 0.6 to about six pounds per square inch.

3. The process of claim 1 wherein the total pressure in the reaction zone is in the range of about 285 to about 425 pounds per square inch absolute.

4. The process of claim 1 wherein the reaction temperature in the reaction zone is in the range of about 90° to about 120° C.

5. The process of claim 1 wherein the molecular oxygen to butane weight ratio is in the range of about 0.1 to about 10:1.

6. The process of claim 1 wherein the molecular oxygen to butane weight ratio is in the range of about 0.3:1 to about 3:1.

7. The process of claim 1 wherein the weight ratio of combined acetic acid and cobalt to butane is in the range of about 0.5:1 to about 15:1.

8. The process of claim 7 wherein the weight percent of cobalt based on the combined weights of acetic acid and cobalt is in the range of about 0.1 to about 10 percent.

9. The process of claim 8 wherein about 10 to about 90 weight percent of the cobalt is in the form of cobaltic ions.

10. The process of claim 1 wherein the weight ratio of combined acetic acid and cobalt to butane is in the range of about 1:1 to about 10:1.

11. The process of claim 10 wherein the weight percent of cobalt based on the combined weights of acetic acid and cobalt is in the range of about one to about five percent.

12. The process of claim 11 wherein about 20 to about 60 weight percent of the cobalt is in the form of cobaltic ions.

13. The process of claim 1 wherein the reaction product is subjected to distillation in a distillation tower having a reboiler temperature of about 25° to about 80° C. to remove an overhead product containing the acetic acid and a bottoms product containing acetic acid having dissolved therein cobaltic ions and recycling said bottoms to constitute the cobalt and acetic acid feed to the reaction zone.

14. The process of claim 13 wherein said reboiler temperature is in the range of about 25° to about 65° C.

15. The process of claim 13 wherein said overhead product contains gases, water and acetic acid and said gases, water and acetic acid are separated from each other.

* * * * *